United States Patent [19]

Schurter et al.

[11] Patent Number: 4,831,148

[45] Date of Patent: May 16, 1989

[54] PROCESS FOR THE PREPARATION OF FLUORINATED PYRIDINE DERIVATIVES

[75] Inventors: Rolf Schurter, Binningen; Urs Siegrist, Möhlin; Hermann Rempfler, Ettingen; Peter Baumeister, Flüh, all of Switzerland

[73] Assignee: Ciba-Geigy Corporation, Ardsley, N.Y.

[21] Appl. No.: 784,017

[22] Filed: Oct. 4, 1985

[30] Foreign Application Priority Data

Oct. 10, 1984 [CH] Switzerland ................. 4855/84

[51] Int. Cl.[4] .......................................... C07D 213/61
[52] U.S. Cl. ..................................... 546/345; 546/311
[58] Field of Search ...................... 546/345, 311

[56] References Cited

U.S. PATENT DOCUMENTS

| 2,563,796 | 5/1948 | Shenk et al. | 546/296 |
| 3,703,521 | 11/1972 | Bondakian | 546/345 |
| 4,031,100 | 6/1977 | Giacobbe | 546/345 |
| 4,071,521 | 1/1978 | Muench | 60/39.281 |
| 4,505,743 | 3/1985 | Schurter et al. | 71/94 |

FOREIGN PATENT DOCUMENTS

| 0083556 | 12/1982 | European Pat. Off. | 546/345 |
| 0104715 | 4/1984 | European Pat. Off. | 546/345 |
| 0097460 | 6/1984 | European Pat. Off. | 546/311 |
| 2409379 | 4/1975 | Fed. Rep. of Germany | 546/345 |
| 3234451 | 4/1984 | Fed. Rep. of Germany | 546/345 |
| 2359106 | 8/1978 | France | 546/345 |
| 81330 | 8/1974 | Japan | 546/345 |
| 0068783 | 6/1978 | Japan | 546/345 |
| 0059283 | 5/1979 | Japan | 546/345 |
| 0219163 | 12/1983 | Japan | 546/345 |
| 1344636 | 8/1974 | United Kingdom | 546/345 |
| 1415825 | 11/1975 | United Kingdom | 546/345 |
| 1534841 | 12/1978 | United Kingdom | 546/345 |
| 2039473 | 5/1980 | United Kingdom | 546/345 |
| 2053189A | 10/1981 | United Kingdom | 546/345 |

OTHER PUBLICATIONS

Berrie, A. H. et al., J. Chem. Soc. 1952 pp. 2042–2046.
Derwent Abstract 54228A/30.
Derwent Abstract 46484B/25.
Derwent Abstract 84-027477/05.
Journal of Fluorine Chemistry, 18(1981) 497–506.
Atkins, P. W. "Physical Chemistry" (1978) pp. 225–228 W. H. Freeman and Company, San Francisco.
Chem. Abstracts, Misaki et al., vol. 81, p. 522 (1974) P.

Roe et al., J. Amer. Chem. Soc., 69, pp. 2443–2444 (1947).
Ferm et al., J. Amer. Chem. Soc., 72, pp. 4809–4811 (1950).

Primary Examiner—Mary C. Lee
Assistant Examiner—Zinna Northington
Attorney, Agent, or Firm—Kevin T. Mansfield; Edward McC. Roberts

[57] ABSTRACT

In accordance with a novel process, 2,3-difluoropyridines of formula I

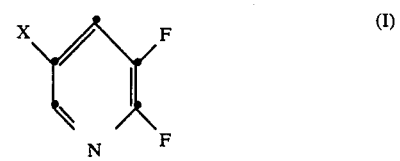

wherein X is halogen or trifluoromethyl, are prepared by diazotising a 3-amino-2-halopyridine of formula II

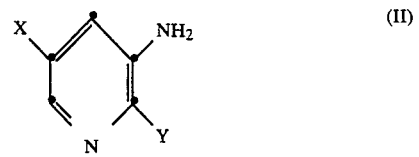

wherein X is as defined for formula I and Y is bromine, chlorine or fluorine, in the presence of hydrogen fluoride, to give a 3-fluoro-2-halopyridine of formula III

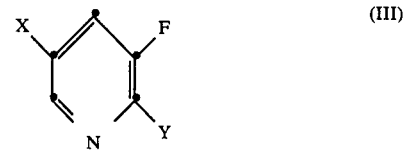

wherein X and Y are as defined for formula II, and treating resultant 3-fluoro-2-halopyridines of formula III, wherein Y is bromine or chlorine, with a fluorinating agent.

The 2,3-difluoropyridines prepared by the novel process are valuable intermediates for the preparation of 2-[4-(3-fluoropyridin-2-yloxy)-phenoxy]propionic acid derivatives which are known as herbicides.

20 Claims, No Drawings

PROCESS FOR THE PREPARATION OF FLUORINATED PYRIDINE DERIVATIVES

The present invention relates to a novel process for the preparation of 2,3-difluoropyridines.

2,3-Difluoropyridines are valuable intermediates for the preparation of herbicides of the class of pyridinyloxyphenoxyalkanecarboxylic acid derivatives. Such herbicides and their biological properties are described in published European patent applications Nos. 83 556 and 97 460.

The processes disclosed in published European patent applications Nos. 97 460 and 104 715 for the preparation of 2,3-difluoropyridines are not very suitable for large-scale industrial application since, on the one hand, expensive chemicals such as caesium fluoride are required at least in stoichiometric amounts and, on the other hand, the required products are only obtained in unsatisfactory yield.

Therefore a need exists for a simple process for the preparation of 2,3-difluoropyridine intermediates, which process makes it possible to obtain these products in high yield using less expensive reagents.

Surprisingly, a novel process for the preparation of these valuable intermediates has been found which substantially satisfies this need.

In accordance with the present invention, it is therefore proposed to prepare 2,3-difluoropyridines of formula I

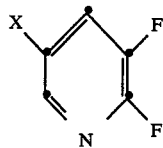

(I)

wherein X is halogen or trifluoromethyl, by diazotising a 3-amino-2-halopyridine of formula II

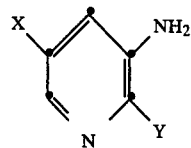

(II)

wherein X is as defined for formula I and Y is bromine, chlorine or fluorine, in the presence of hydrogen fluoride, to give a 3-fluoro-2-halopyridine of formula III

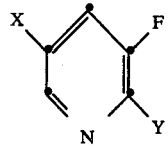

(III)

wherein X and Y are as defined for formula II, and treating resultant 3-fluoro-2-halopyridines of formula III, wherein Y is bromine or chlorine, with a fluorinating agent.

In the formula definitions, halogen is fluorine, chlorine, bromine or iodine, preferably fluorine, chlorine or bromine, with chlorine being most preferred.

The process of the present invention is preferably employed to prepare compounds of formula I, wherein X is chlorine or trifluoromethyl. Accordingly, it is preferred to use starting materials of formula II and so to obtain intermediates of formula III, in which formulae X is chlorine or trifluoromethyl. For carrying out the process, it is advantageous if substituent Y in the starting materials and intermediates of formulae II and III is chlorine or fluorine. Therefore the compounds of formula II, wherein X is chlorine or trifluoromethyl and Y is chlorine or fluorine, are particularly suitable for carrying out the process of the invention. Accordingly, the intermediate of formula III is obtained, wherein X is chlorine or trifluoromethyl and Y is chlorine.

When using 3-amino-2-halopyridines of formula II, wherein Y is fluorine, the 2,3-difluoropyridines of formula I are obtained direct by diazotising in the presence of hydrogen fluoride. When using 3-amino-2-halopyridines of formula II, wherein Y is chlorine or bromine, the process of the present invention is generally carried out in two successive reation steps in such a manner that in the first step the amino function in the 3-position is diazotised with a nitrite and replaced by fluorine and in the second step the chlorine or bromine atom in the 2-position is replaced by fluorine by means of a fluorinating agent.

The diazotisation in the first reaction step is advantageously carried out in the presence of an excess of hydrogen fluoride. The minimum requisite is one equivalent of hydrogen fluoride. In the first step, an inert solvent may be used, e.g. sulfolane, dimethyl sulfoxide, an amide such as dimethylformamide, dimethylacetamide or dimethylpropylene urea, or an ether such as tetraethylene glycol dimethyl ether. It is, however, particularly advantageous to carry out the reaction in liquid hydrogen fluoride. On account of the low boiling point of hydrogen fluoride, it is advantageous to carry out the reaction in an autoclave in order to be able to raise the reaction temperature to above the boiling point of hydrogen fluoride if desired. The reaction temperature is generally in the range from $-20°$ C. to $+100°$ C., preferably from $-10°$ C. to $+70°$ C. At the beginning of the reaction it is advantageous to select a temperature in the lower half of the indicated range and then to raise it in order to complete the reaction. The pressure in this reaction corresponds to the pressure existing at the chosen temperature.

Alternatively, the reaction may be advantageously carried out in a mixture of the required amount of hydrogen fluoride and one of the above-mentioned solvents. In this case, the reaction temperature is selected such that diazonium fluoride forms and simultaneously nitrogen splits off. The use of this inert solvent makes it possible to lower the vapour pressure of the hydrogen fluoride. On account of the concomitant decrease in pressure, the reaction can be carried out under normal pressure, thus resulting in a reduction of operating costs of the reactor. In this mode of carrying out the process, the reaction temperature is in the range from $0°$ C. to $+70°$ C.

Nitrites are normally used as diazotising agents, e.g. sodium or potassium nitrite, and also dinitrogen trioxide, nitric acid, nitrosyl halides or complexes of nitrosyl halides with the reactant hydrogen fluoride. Sodium nitrite or dinitrogen trioxide are preferred.

The substitution of a chlorine or bromine atom in the 2-position of the pyridine ring by fluorine is generally carried out in an inert polar aprotic solvent such as dimethyl sulfoxide, dimethyl sulfone, N-methylpyrrolidinone, dimethylacetamide, dimethylformamide, sulfolane or hexamethylphosphoric triamide. The reaction temperatures are generally in the range from 80° C. to 220° C., preferably from 120° C. to 170° C. Potassium fluoride is a particularly suitable fluorinating agent. It is used in at least an equimolar amount. The use of a fluorination catalyst is also of advantage when carrying out the reaction. Such catalysts are, on the one hand, heavy alkali metal fluorides such as caesium fluoride and, on the other hand, crown ethers such as 12-crown-4, 15-crown-5, 18-crown-6, dibenzo-18-crown-6, dicyclohexano-18-crown-6 or dicyclohexano-24-crown-8, or also various substituted ammonium fluorides such as tetrabutylammonium fluoride or triethylbenzylammonium fluoride. These catalysts may be added to the fluorinating agent individually or as mixtures. It is convenient to add 0.001 to 0.1 mol of catalyst per mol of starting material to be fluorinated.

The diazotisation in the presence of hydrogen fluoride and the substitution of chlorine or bromine in the 2-position of the pyridine ring by fluorine may be carried out either in succession in the same reactor without isolation of the intermediate or individually in different reactors with isolation of the intermediate of formula III.

The starting materials and intermediates of formulae II and III are known if X is trifluoromethyl.

The compounds of formulae II and III, wherein X is halogen, are novel and have been specifically developed and prepared in connection with the process of the present invention. These novel compounds, i.e. compounds of subformula IIa

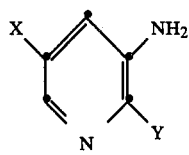
(IIa)

wherein X is halogen and Y is bromine, chlorine or fluorine, and compounds of subformula IIIa

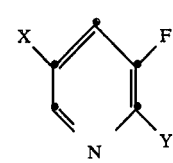
(IIIa)

whwerein X is halogen and Y is bromine or chlorine, therefore constitute an object of the present invention.

The compounds of formula II are prepared from the corresponding 3-nitropyridine derivatives of formula IV

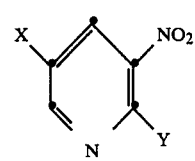
(IV)

wherein X and Y are as defined for formula II, by catalytic reduction with hydrogen. Customary reaction conditions which are known to the skilled person and are applied in the preparation of compounds of formula II are:

hydrogen atmospheric pressures in the range from 1 to 20 bar, preferably from 1 to 5 bar;

reaction temperatures in the range from −20° C. to +50° C., preferably from 0° C. to 30° C.;

inert solvent selected from the series consisting of: ethers, esters, alcohols or hydrocarbons; preferably: tetrahydrofuran, dioxane, diethyl ether, ethyl acetate, methanol, ethanol, pentane, cyclohexane or benzene; and hydrogenation catalysts selected from the 8th subgroup of the Periodic Table: nickel, palladium or platinum in commercially available form, e.g. Raney nickel, palladium on carbon, platinum oxide or platinum black.

The 3-nitropyridines of formula IV employed are known or may be prepared by processes which are known per se.

The valuable herbicides of the class of 2-[4-(3-fluoropyridin-2-yloxy)phenoxy]propionic acid derivatives are obtained from the 2,3-difluoropyridines prepared by the process of the present invention for example in accordance with the reactions as shown in the following Scheme 1:

Scheme 1

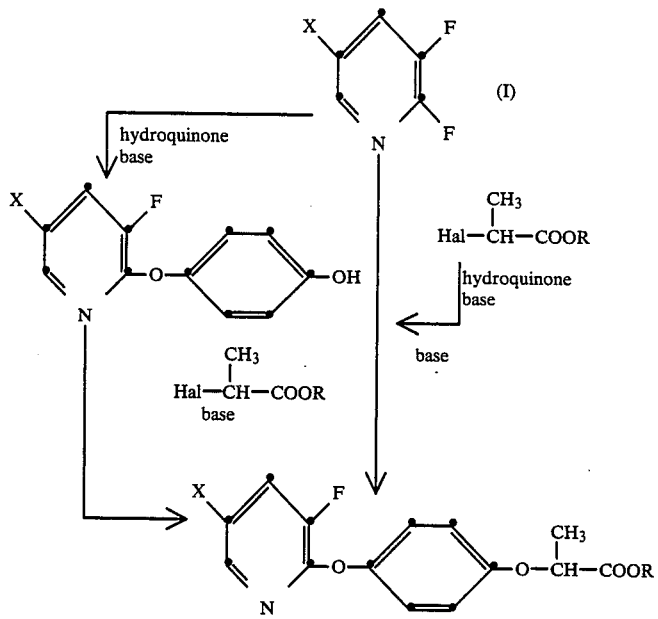

Hal is halogen, preferably chlorine or bromine, R is any organic radical.

The present invention is illustrated in more detail by the following Examples. Any of Examples P4 to P8 may replace the reaction of step b of Example P1, and Example P9 may replace that of steps b and c of Example P1.

PREPARATORY EXAMPLES

Example P1: 5-Chloro-2,3-difluoropyridine (a) 3-Amino-2,5-dichloropyridine 26.0 g of Raney nickel catalyst are washed with ethanol and then added to a solution of 129.2 g (0.69 mol) of 2,5-dichloro-3-nitropyridine in 1300 ml of dioxane. This mixture is hydrogenated with hydrogen under normal pressure and at a temperature in the range from 20° to 35° C. After reaction of 20% of the required amount of hydrogen, a further 30.0 g of Raney nickel catalyst are added to the reaction mixture. After a hydrogenation period of 22 hours, the catalyst is removed, the solvent is evaporated off and the residue is crystallised from ethyl acetate/hexane, affording 84.9 g (78% of theory) of 3-amino-2,5-dichloropyridine, m.p. 129°–132° C.

(b) 2,5-dichloro-3-fluoropyridine

A Monel autoclave is charged with 450 ml (22.5 mol) of hydrogen fluoride and then 163 g (1.0 mol) of 3-amino-2,5-dichloropyridine are added at a temperature in the range from −5° to −1° C. Over 1½ hours, 82.8 g (1.2 mol) of sodium nitrite are introduced into this solution. After the reaction mixture has been stirred at the same temperature for 1½ hours, the temperature is raised stepwise to +60° C. When the evolution of gas ceases, the hydrogen fluoride is evaporated off and the residue is taken up in methylene chloride and the resultant solution is poured into ice water. The two-phase mixture is neutralised with concentrated ammonia solution. The organic phase is separated and the aqueous phase is extracted three times with methylene chloride. The combined organic phases are washed with water, dried over magnesium sulfate, treated with active carbon, filtered through silica gel and concentrated by evaporation, affording 141.5 g (85% of theory) of 2,5-dichloro-3-fluoropyridine, m.p. 38°–39° C.

(c) 64.6 g (1.11 mol) of potassium fluoride and 11.25 g (0.074 mol) of caesium fluoride are suspended in 240 ml of sulfolane and the suspension is heated to 140° C. 50 mol of sulfolane are distilled off by decreasing the pressure and then 61.4 g (0.37 mol) of 2,5-dichloro-3-fluoropyridine and 1.45 g (0.0055 mol) of 18-crown-6 in 20 ml of sulfolane are added to the suspension. This reaction mixture is stirred for 35 hours at 140° C. and then taken up in ice water. The product is isolated from the aqueous mixture either by extraction with ether or by steam distillation, affording 48.7 g (88% of theory) of 5-chloro-2,3-difluoropyridine, b.p. 65°–66° C. at 133 mbar.

Example P2: Methyl 2-[4-(5-chloro-3-fluoropyridin-2-yloxy)phenoxy]-propionate

A solution of 14.95 g (0.10 mol) of 5-chloro-2,3-difluoropyridine in 30 ml of acetonitrile is added dropwise to a mixture of 21.6 g (0.11 mol) of methyl 2-(4-hydroxyphenoxy)propionate, 15.2 g (0.11 mol) of potassium carbonate, 1.45 g (0.0055 mol) of 18-crown-6 and 100 ml of acetonitrile and the reaction mixture is then heated for 40 hours to a temperature in the range from 50° to 60° C. The mixture is taken up in ice water, the organic phase is separated, the aqueous phase is extracted three times with ethyl acetate and the combined organic phases are dried and concentrated by evaporation, affording an oily residue which for purification is dissolved in a mixture of hexane and ethyl acetate and filtered through silica gel. The solvent is evaporated off, affording from the filtrate 20.4 g (63% of theory) of methyl 2-[4-(5-chloro-3-fluoropyridin-2-yloxy)phenoxy]propionate, m.p. 58°–59° C.

Example P3: 2,3-Difluoro-5-trifluoromethylpyridine (a) 3-Amino-2-chloro-5-trifluoromethylpyridine 12.3 g (0.0543 mol) of 2-chloro-3-nitro-5-trifluoromethylpyridine are dissolved in 250 ml of ethanol, then 2.4 g of Raney nickel catalyst are added and the reaction mixture is hydrogenated with hydrogen under normal pressure and at a temperature in the range from 20° to 25° C. After a hydrogenation period of 28 hours, the catalyst is removed, the solvent is distilled off and the residue is crystallized from ethyl acetate/hexane, affording 9.0 g (84% of theory) of 3-amino-2-chloro-5-trifluoromethylpyridine, m.p. 94°–95° C.

(b) 2-Chloro-3-fluoro-5-trifluoromethylpyridine A Monel autoclave is charged with 120 g (6.0 mol) of hydrogen fluoride and then 27.0 g (0.137 mol) of 3-amino-2-chloro-5-trifluoromethylpyridine are added at a temperature in the range from −5° C. to 0° C. Over 1 hour, 10.35 g (0.15 mol) of sodium nitrite are introduced into this solution. After the reaction mixture has been stirred at the same temperature for 2 hours, the temperature is raised stepwise to 50° C. When the evolution of nitrogen ceases, the hydrogen fluoride is evaporated off, the residue is taken up in methylene chloride and the resultant solution is poured into ice water. With good cooling the two-phase mixture is neutralised with concentrated ammonia solution. The organic phase is separated and the aqueous phase is extracted three times with methylene chloride. The combined organic phases are washed with water, dried over magnesium sulfate and filtered through a small amount of silica gel. The solvent is distilled off and the resultant product is then distilled, b.p. 113° C. (975 mbar).

(c) 47.7 g (0.82 mol) of potassium fluoride and 10.0 g (0.065 mol) of caesium fluoride are suspended in 300 ml of sulfolane and the suspension is heated to 140° C. 60 ml of sulfolane are distilled off by decreasing the pressure and subsequently 65.6 g (0.329 mol) of 2-chloro-3-fluoro-5-trifluoromethylpyridine and 1.3 g (0.004 mol) of 18-crown-6 are added. The reaction mixture is stirred for 48 hours at 140° C. and subsequently distilled by introducing steam. The oil is separated and the aqueous phase is extracted twice with a small amount of ether. The organic phases are purified, dried with a small amount of magnesium sulfate and filtered. Distillation affords 54.8 g (91% of theory) of 2,3-difluoro-5-trifluoromethylpyridine, b.p. 100°–102° C. (980 mbar).

Example P4: 2,5 Dichloro-3-fluoropyridine

A 500 ml polytetrafluoroethylene reactor equipped with stirrer, thermometer and reflux condenser is charged with 120 g of hydrogen fluoride. A solution of 40.7 g (0.25 mol) of 3-amino-2,5-dichloropyridine in 60 ml of dimethyl sulfoxide is added dropwise at a temperature in the range from 0° C. to +10° C. Then 20.7 g (0.3 mol) of sodium nitrite are introduced into this solution at +40° C. The resultant nitrogen is removed from the reactor through the reflux condenser. Gas evolution ceases after 4 hours at +40° C. 150 ml of methylene chloride are added to the reaction mixture which is then poured into ice water. The two-phase mixture is neutralised with concentrated ammonia solution. The organic phase is separated and the aqueous phase is extracted three times with methylene chloride. The combined organic phases are washed with water, dried over sodium sulfate and filtered through silica gel. The solution is separated by distillation, affording 36.5 g (88% of theory) of 2,5-dichloro-3-fluoropyridine.

Example P5: 2,5-Dichloro-3-fluoropyridine

A 500 ml polytetrafluoroethylene reactor equipped with stirrer, thermometer and reflux condenser is charged with 60 g of hydrogen fluoride. A solution of 40.7 g (0.25 mol) of 3-amino-2,5-dichloropyridine in 100 ml of sulfolane is added dropwise at a temperature in the range from 0° C. to +10° C. Then 20.7 g (0.3 mol) of sodium nitrite are introduced into this solution at +50° C. The resultant nitrogen is removed from the reactor through the reflux condenser. Gas evolution ceases after 2 hours at +50° C. 150 ml of methylene chloride are added to the reaction mixture which is then poured into ice water. The two-phase mixture is neutralised with concentrated ammonia solution. The organic phase is separated and the aqueous phase is extracted several times with methylene chloride. The combined organic phase are dried over sodium sulfate and concentrated by evaporation. The solution of the sulfolane product is separated by distillation, affording 34.3 g (82.6% of theory) of 2,5-dichloro-3-fluoropyridine.

Example P6: 2,5-Dichloro-3-fluoropyridine

A 500 ml polytetrafluoroethylene reactor equipped with stirrer, thermometer and reflux condenser is charged with 120 g of hydrogen fluoride. A solution of 40.7 g (0.25 mol) of 3-amino-2,5-dichloropyridine in 100 ml of dimethylformamide is added dropwise at a temperature in the range from 0° C. to +10° C. Then 20.7 g (0.3 mol) of sodium nitrite are introduced into this solution at 55° C. The resultant nitrogen is removed from the reactor through the reflux condenser. Gas evolution ceases after 2 hours at +50° C. 150 ml of methylene chloride are added to the reaction mixture wich is then poured into ice water. The two-phase mixture is neutralized with concentrated ammonia solution. The organic phase is separated and the aqueous phase is extracted several times with methylene chloride. The combined organic phases are dried over sodium sulfate and concentrated by evaporation. The crude product is purified by distillation, affording 37.9 g (91.4% of theory) of 2,5-dichloro-3-fluoropyridine.

Example P7: 2,5-Dichloro-3-fluoropyridine

A 500 ml polytetrafluoroethylene reactor equipped with stirrer, thermometer and reflux condenser is charged with 120 g of hydrogen fluoride. A solution of 40.7 g (0.25 mol) of 3-amino-2,5-dichloropyridine in 100 ml of dimethylacetamide is added dropwise at a temperature in the range from 0° to +10° C. Then 20.7 g (0.3 mol) of sodium nitrite are introduced into this solution at 55° C. The resultant nitrogen is removed from the reactor through the reflux condenser. Gas evolution ceases after 2½ hours at 55° C. 150 ml of methylene chloride are added to the reaction mixture which is then poured into ice water. The two-phase mixture is neutralised with concentrated ammonia solution. The organic phase is separated and the aqueous phase is extracted several times with methylene chloride. The combined organic phases are dried over sodium sulfate and concentrated by evaporation. The crude product is purified by distillation, affording 36.4 g (87.8% of theory) of 2,5-dichloro-3-fluoropyridine.

Example P8: 2,5-Dichloro-3-fluoropyridine

A 500 ml polytetrafluoroethylene reactor equipped with stirrer, thermometer and reflux condenser is charged with 120 g of hydrogen fluoride. A solution of 40.7 g (0.25 mol) of 3-amino-2,5-dichloropyridine in 60 ml of dimethyl sulfoxide is added dropwise at a temperature in the range from 0° C. to +10° C. Over 1½ hours, 24.7 g (0.325 mol) of dinitrogen trioxide are introduced into this solution at a temperature in the range from +°50 C. to 60° C. The resultant nitrogen is removed from the reactor through the reflux condenser. Gas evolution ceases after a total of 3 hours at 50° C. to 60° C. 150 ml of methylene chloride are added to the reaction mixture which is then poured into ice water. The two-phase mixture is neutralised with concentrated ammonia solution. The organic phase is separated and the aqueous phase is extracted several times with methylene chloride. The combined organic phases are dried over sodium sulfate. The solution is separated by distillation, affording 38.2 g (92.1% of theory) of 2,5-dichloro-3-fluoropyridine.

Example P9: 5-Chloro-2,3-difluoropyridine

A 500 ml polytetrafluoroethylene reactor equipped with stirrer, thermometer and reflux condenser is charged with 120 g of hydrogen fluoride. A solution of 40.7 g (0.25 mol) of 3-amino-2,5-dichloropyridine in 100 ml of sulfolane is added dropwise at a temperature in the range from 0° C. to +10° C. Then 20.7 g (0.3 mol) of sodium nitrite are introduced into this solution at +50° C. The resultant nitrogen is removed from the reactor through reflux condenser. Gas evolution ceases after 2 hours at +50° C. 150 ml of methylene chloride are added to the reaction mixture which is then poured into ice water. The two-phase mixture is neutralised with ammonia solution. The organic phase is separated and dried over sodium sulfate. The solvent is distilled off and then 200 ml of sulfolane, 166 g (2.879 mol) of potassium fluoride and 2 g of tetrabutylammonium bromide are added to the mixture of sulfolane and the product. This reacton mixture is stirred for 7 hours at 179° C. The product is subsequently distilled off directly from the sulfolane solution. The crude product is purified by distillation, affording the 5-chloro-2,3-difluoropyridine, b.p. 137°–139° C.

Example P10: 3-Amino-5-chloro-2-fluoropyridine 7.5 g (0.042 mol) of 5-chloro-2-fluoro-3-nitropyridine are dissolved in 80 ml of ethanol. This solution is hydrogenated with hydrogen, in the presence of 1 g of Raney nickel catalyst, under normal pressure and at a temperature in the range from 20° to 25° C. After a hydrogenation period of 20 hours, the catalyst is removed and the solvent is evaporated off. The residue is taken up in ethyl acetate and the resultant solution is filtered through a layer of silica gel. The solvent is evaporated off and the residue is triturated in hexane. The precipitate is subsequently filtered and dried, affording 4.7 g (76%) of 3-amino-5-chloro-2-fluoropyridine, m.p. 74° C.

The intermediates of formulae II and III of the process of the present invention which are listed in the following Tables are obtained in analogous manner.

TABLE 1

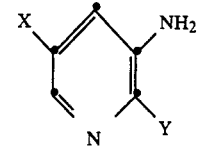

| X | Y |
| --- | --- |
| Cl | Br |
| Br | Cl |
| Br | Br |
| F | Cl |
| F | Br |
| CF₃ | F |
| CF₃ | Br |

TABLE 2

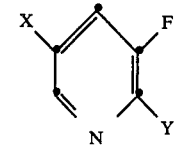

| X | Y |
| --- | --- |
| Cl | Br |
| Br | Cl |
| Br | Br |
| F | Cl |
| F | Br |
| CF₃ | F |
| CF₃ | Br |

What is claimed is:
1. A process for the preparation of a 2,3-difluoropyridine of formula I

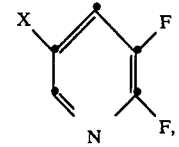
(I)

wherein X is halogen or trifluoromethyl, from a 3-amino-2-halopyridine of formula II

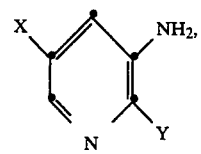
(II)

wherein X is as defined for formula I and Y is bromine, chlorine or fluorine, which process comprises adding to a solution of the 3-aminopyridine of formula II in sulfolane, dimethyl sulfoxide, dimethylformamide, dimethylacetamide, dimethylpropylene urea or tetraethylene glycol dimethylether and in the presence of hydrogen fluoride, at the decomposition temperature of the diazonium salt formed, a diazotization agent selected from sodium nitrite, potassium nitrite, dinitrogen trioxide and nitrosyl halides, at such a rate that the diazonium salt formed is at low concentration, and, when Y is formula II is chlorine or bromine, reacting the 3-fluoro-2-halopyridine of formula III

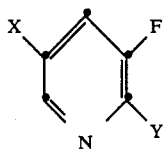

wherein X is as defined for formula II, and Y is chlorine or bromine, with a fluorinating agent and in the presence of absence of a catalyst.

2. A process according to claim 1, wherein X is chlorine or trifluoromethyl.

3. A process according to claim 1, wherein Y is fluorine or chlorine.

4. A process according to claim 1, wherein Y is chlorine.

5. A process according to claim 1, wherein X is chlorine or trifluoromethyl and Y is chlorine or fluorine.

6. A process according to claim 1, wherein X is chlorine or trifluoromethyl and Y is chlorine.

7. A process according to claim 1, which comprises the use of potassium fluoride as fluorinating agent.

8. A process according to claim 1, which comprises the use of potassium fluoride as fluorinating agent in the presence of a catalyst.

9. A process according to claim 8, which comprises the use of caesium fluoride or a crown ether or mixture thereof as catalyst.

10. A process according to claim 1, which comprises carrying out the diazotisation with an excess of hydrogen fluoride.

11. A process according to claim 10, which comprises carrying out the diazotisation in hydrogen fluoride in an autoclave at temperature up to +100° C. and under the existing pressure.

12. A process according to claim 11, which comprises carrying out the diazotisation and decomposition at temperature up to +70° C. and under normal pressure.

13. A process according to claim 1, which comprises the use of sodium nitrite or dinitrogen trioxide as diazotising agent.

14. A process according to claim 1, which comprises the use of dimethyl sulfoxide, sulfolane, dimethylacetamide, or dimethylformamide as solvent.

15. A process according to claim 1, which comprises carrying out the substitution of chlorine or bromine in the 2-position of the pyridine ring by fluorine at a temperature in the range from 80° C. to 220° C.

16. A process according to claim 15, wherein the temperature is in the range from 120° C. to 170° C.

17. A process according to claim 1, which comprises carrying out the substitution of chlorine or bromine in the 2-position of the pyridine ring by fluorine directly after the diazotisation of the 3-amino-2-halopyridine of formula II, without isolation of the 3-fluoro-2-halopyridine of formula III and at a temperature in the range from 80° C. to 170° C.

18. A process according to claim 1, which comprises adding to the fluorination agent potassium fluoride 0.001 mol to 0.1 mol of fluorination catalyst per mol of starting material to be fluorinated.

19. A process according to claim 1, which comprises carrying out the substitution of chlorine or bromine in the 2-position of the pyridine ring by fluorine in dimethyl sulfoxide, sulfolane, dimethylformamide or dimethylacetamide with potassium fluoride in the presence of 0.001 mol to 0.1 mol of caesium fluoride per mol of starting material and at a temperature in the range from 120° C. to 170° C.

20. A process according to claim 1, which comprises carrying out the diazotisation using sodium nitrite or dinitrogen trioxide in hydrogen fluoride with an inert solvent at temperature up to +70° C. and under normal pressure, and carrying out the substitution of chlorine or bromine in the 2-position of the pyridine ring by fluorine in dimethyl sulfoxide or sulfolane with potassium fluoride in the presence of 0.001 mol to 0.1 mol of caesium fluoride per mol of starting material and at a temperature in the range from 120° to 170° C.

* * * * *